United States Patent
DeGroot et al.

(10) Patent No.: US 7,174,208 B2
(45) Date of Patent: Feb. 6, 2007

(54) SLOW RISE DEFIBRILLATION WAVEFORMS TO MINIMIZE STORED ENERGY FOR A PULSE MODULATED CIRCUIT AND MAXIMIZE CHARGE TRANSFER TO MYOCARDIAL MEMBRANE

(75) Inventors: Paul J. DeGroot, Brooklyn Park, MN (US); Paul A. Belk, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 439 days.

(21) Appl. No.: 10/693,763

(22) Filed: Oct. 24, 2003

(65) Prior Publication Data

US 2004/0116967 A1 Jun. 17, 2004

Related U.S. Application Data

(60) Provisional application No. 60/430,797, filed on Dec. 3, 2002.

(51) Int. Cl.
*A61N 1/39* (2006.01)
(52) U.S. Cl. .............................. 607/7; 607/5
(58) Field of Classification Search ................... 607/5, 607/7
See application file for complete search history.

(56) References Cited

U.S. PATENT DOCUMENTS

| | | | |
|---|---|---|---|
| 4,328,808 A | 5/1982 | Charbonnier et al. |
| 4,574,810 A | 3/1986 | Lerman |
| 4,577,633 A | 3/1986 | Berkovits et al. |
| 4,587,970 A | 5/1986 | Holley et al. |
| 4,727,380 A | 2/1988 | Miura et al. |
| 4,727,877 A | 3/1988 | Kallok |
| 4,768,512 A | 9/1988 | Imran |
| 4,771,781 A | 9/1988 | Lerman |
| 4,800,883 A | 1/1989 | Winstrom |
| 4,830,006 A | 5/1989 | Haluska et al. |
| 4,834,100 A | 5/1989 | Charms |
| 4,880,005 A | 11/1989 | Pless et al. |
| 4,949,719 A | 8/1990 | Pless et al. |
| 4,953,551 A | 9/1990 | Mehra et al. |
| 5,088,489 A | 2/1992 | Lerman |
| 5,111,813 A | 5/1992 | Charbonnier et al. |
| 5,163,427 A | 11/1992 | Keimel |
| 5,165,162 A | 11/1992 | Charles |

(Continued)

FOREIGN PATENT DOCUMENTS

EP 0 813 892 A2 12/1997

(Continued)

*Primary Examiner*—Robert Pezzuto
*Assistant Examiner*—Shevon Johnson

(57) ABSTRACT

The present invention provides structures and methods for delivering a complex slow-rise defibrillation waveform wherein in lieu of the simple truncation of prior art defibrillation waveforms, when a predetermined amplitude is reached for an ascending waveform (e.g., a ramp waveform), the waveform transitions to an exponential decay portion for a period of time and at the expiration of the period of time, a truncation occurs. In the event that a first complex bi-phasic ramp wave form is implemented, a second opposite polarity waveform may be delivered. Said second waveform is preferably of similar shape to the first waveform, but of a less magnitude amplitude, although the second waveform may comprise a traditional waveform. The implementation and feasibility of the waveforms according to the present invention in an ICD or an AED is relatively simple while providing significant advantages not previously known or used in the prior art.

21 Claims, 11 Drawing Sheets

U.S. PATENT DOCUMENTS

| | | |
|---|---|---|
| 5,184,616 A | 2/1993 | Weiss |
| 5,188,105 A | 2/1993 | Keimel |
| 5,201,865 A | 4/1993 | Kuehn |
| 5,481,238 A | 1/1996 | Carsten et al. |
| 5,549,643 A | 8/1996 | Kroll et al. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,629,842 A | 5/1997 | Johnson et al. |
| 5,645,573 A | 7/1997 | Kroll et al. |
| 5,725,560 A | 3/1998 | Brink |
| 5,733,310 A | 3/1998 | Lopin et al. |
| 5,735,879 A | 4/1998 | Gliner et al. |
| 5,749,904 A | 5/1998 | Gliner et al. |
| 5,749,905 A | 5/1998 | Gliner et al. |
| 5,769,872 A | 6/1998 | Lopin et al. |
| 5,776,166 A | 7/1998 | Gliner et al. |
| 5,797,968 A | 8/1998 | Lopin et al. |
| 5,800,462 A | 9/1998 | Lopin et al. |
| 5,800,463 A | 9/1998 | Lopin et al. |
| 5,803,927 A | 9/1998 | Cameron et al. |
| 5,836,978 A | 11/1998 | Gliner et al. |
| 5,904,706 A | 5/1999 | Ayati et al. |
| 5,908,442 A | 6/1999 | Brewer et al. |
| 5,978,706 A | 11/1999 | Brewer et al. |
| 5,991,658 A | 11/1999 | Brewer et al. |
| 6,047,212 A | 4/2000 | Gliner et al. |
| 6,096,063 A | 8/2000 | Lopin et al. |

FOREIGN PATENT DOCUMENTS

| | | |
|---|---|---|
| WO | WO 92/18198 | 10/1992 |

Example 1 (Single Toroid, Magnetics Core Selector Chart Method L = 14 μH)

LI$^2$ = 12 from selector chart choose 58350-A2
58350-A2 perm. 125μ A$_L$ = 105  l = 5.88 cm

N = 1000*(0.014/105)$^{0.5}$ = 11.5

H = (0.4*PI*11.5*40)/5.88 = 99 (design manual table: ~33% perm. At Ip)
So Inductance falls to 0.33*14μH = 4.6 μH at 40 Amps Volume = 5.2 cc (diameter = 24.6 mm, length = 10.9 mm)

Example 2 (Single Toroid, L = 14 μH)

58043-A2  perm. 14μ   A$_L$ = 7   l = 2.38 cm

N = 1000*(0.014/7)$^{0.5}$ = 44.7

H = (0.4*PI*44.7*40)/2.38 = 944 (design manual table: ~71% perm at Ip)
So Inductance falls to 0.71*14μ = 9.9 μH at 40 Amps Volume = 0.59 cc (diameter = 11.2 mm, length = 5.96 mm)

Example 3 (2 stacked toroids, L = 14 μH)

58273-A2  perm. 14μ   A$_L$ = 12   l = 1.363

N = 1000*[0.014//2*12)]$^{0.5}$ = 24

H = (0.4*PI*24*30)/1.363 = 884 (design manual table: ~72% perm. at Ip)
So Inductance falls to 0.72*14 μH = 10.0 μH at 40 Amps Volume = 0.53 cc (diameter = 7.6 mm, length = 11.7 mm)

FIG. 8

SLOW RISE DEFIBRILLATION WAVEFORMS TO MINIMIZE STORED ENERGY FOR A PULSE MODULATED CIRCUIT AND MAXIMIZE CHARGE TRANSFER TO MYOCARDIAL MEMBRANE

CROSS REFERENCE TO RELATED APPLICATION

This application claims the benefit of provisional U.S. patent application Ser. No. 60/430,797 and hereby incorporates by reference a prior non-provisional U.S. patent application entitled, "Control of Arbitrary Waveforms for Constant Delivered Energy," filed on 3 Dec. 2002 as application Ser. No. 10/308,832.

FIELD OF THE INVENTION

The present invention relates generally to cardiac stimulators. Specifically, this invention relates to the generation of defibrillation waveforms for delivery to cardiac tissue to interrupt ventricular fibrillation and restore a normal cardiac rhythm. More specifically, the present invention provides an apparatus and method of efficiently delivering defibrillation energy to a portion (or membrane) of myocardial tissue. The present invention may be used in conjunction with implantable medical devices, such as an implantable cardioverter-defibrillator (ICD) or external devices, such as an automated external defibrillator (AED).

BACKGROUND OF THE INVENTION

Prior art ICD and AED devices deliver therapeutic defibrillation energy to a patient by discharging one or more charged capacitors through electrodes that electrically couple to the patient's heart. In those ICDs, total energy is limited by controlling the amount of stored energy on the capacitor(s), which, in turn, limits the charge voltage. Typically, the waveform used to deliver the defibrillation energy is truncated when voltage on the capacitor decays to a known value. The resulting waveform exhibits an exponential decay with a constant tilt. The tilt is the percentage by which the waveform voltage decays from start to end.

Waveforms used in implantable defibrillators to defibrillate a patient have been, for the most part, simple truncated exponential waveforms. Truncated exponential waveforms are generated by charging the capacitor(s) and discharging it through the total impedance, which includes the impedance of the patient and the leads used to deliver the waveform. Simple truncation has been used clinically because of the concern that the long, low tail end of a non-truncated exponential waveform might re-induce fibrillation.

In spite of its technological limitations, manufacturers of implantable cardioverter-defibrillators (ICDs) continue to use truncated exponential waveforms for clinical settings. Moreover, ICD manufacturers have long produced ICDs with programmable shock strengths. The strength of the shock required to defibrillate, is controlled by the time constant (TC) and tilt (T) of the truncated exponential waveform. TC is defined as the time required for the shock voltage to decrease to a preset percentage of its starting value and tile is the percentage of leading edge voltage remaining at the trailing edge of the waveform. Altering the duration of the waveform while maintaining the same TC will change tilt. Altering TC while holding waveform duration constant will change tilt. Tilt can additionally be changed by modifying both TC and waveform duration.

Monophasic truncated exponential waveforms were generally used until biphasic truncated exponential waveforms were introduced. Biphasic waveforms are created by a switch in the capacitance that reverses the polarities delivered to the electrodes during delivery of the shock pulse. Some biphasic waveforms are thought to have lower defibrillation thresholds (DTs), compared to monophasic waveforms. This is particularly true when the first phase of the biphasic waveform delivers more energy than the second phase.

In addition to the types of waveform used, the determination of which electrode functions as the anode in the right ventricle appears to lower the DT when a monophasic waveform is used. Such a determination of the electrode polarity, however, appears to have little influence when biphasic waveforms are used. Clinicians, however, generally err on the side of caution and program the right ventricular electrode as the anode when using a biphasic waveform.

A published study by Huang et al., "Defibrillation Waveforms" in *Nonpharmacological Therapy of Arrhythmias for the 21$^{st}$ Century: The State of the Art*, Futura, 1998 concludes: "Thus, the (truncated exponential) biphasic waveform appears to be more efficacious for defibrillation than the (truncated exponential) monophasic waveform for internal as well as external defibrillation and for ventricular as well as atrial defibrillation." This same study, in its opening paragraph, states: "Schuder, et al (in *Circ Res*, 1966, 19: 689–694) have shown that for external defibrillation in the dog, a waveform consisting of an ascending ramp has a much higher success rate for defibrillation than a descending ramp waveform of the same strength." Despite this fact, there has been little research and/or implementation of the ascending ramp. This may be because waveforms similar to the descending ramp are much easier to generate, the descending ramp type of waveform is used clinically even though it is much less efficient for defibrillation.

In U.S. Pat. No. 5,725,560, Brink describes a method of delivering arbitrary waveforms with a computer-controlled system. The basic energy converter topology disclosed is a buck, or step-down, type of power converter with a pulse width modulation control scheme. This type of power converter is a common topology used in the field of energy conversion. The circuitry developed in the '560 patent is implemented as a full bridge (H-bridge) dc—dc converter that enables biphasic waveforms. The system monitors the voltage and current delivered to the patient and uses these parameters as a control feedback.

Weiss, in U.S. Pat. No. 5,184,616, teaches an arbitrary waveform circuit for use in ICDs. As in the '560 patent, a switching power converter is used with a full bridge (H-bridge) implementation. The '616 patent has a control scheme with a predetermined pulse width or duty cycle for each switching cycle during delivery of the waveform. In some cases, an impedance measurement is required to determine the proper timing. This impedance measurement uses a constant current source by applying current to the patient and then computing measured applied voltage over applied current. A feedback element receives signal information from the output of the filter circuit. Based on this input, the circuit assumes that the output to the patient is monitored so that the microprocessor can make adjustments to the shock control, charge control, and dump control lines.

Imran, in U.S. Pat. No. 4,768,512, describes a method of delivering a truncated exponential waveform that is "chopped" or comprised of a train of high frequency, exponentially decaying pulses delivered from a storage capacitor. In this patent, when a feedback signal on the patient load drops below a reference voltage, the output voltage is disabled, resulting in a waveform truncation.

Brewer, et al. have been granted a number of patents relating to the control and delivery of various defibrillation waveforms. For example, In U.S. Pat. No. 5,908,442, Brewer et al. discloses a method of delivering biphasic truncated damped sine wave shocks. Two discharge circuits that operate in succession allow delivery of biphasic wave shocks. The truncation time of the shock is determined using the Blair equivalent circuit model of defibrillation together with knowledge of distributed impedances of the chest wall, thorax, lung, and heart. This method requires that the total patient impedance be known before shock delivery.

Brewer et al., in U.S. Pat. No. 5,991,658, describes a method of continuously determining the tilt of a truncated exponential waveform based on repeated discrete measurements of the impedance or resistance of the patient. When the storage capacitors decay to the optimal tilt (based on defibrillation efficacy models) equals the computed tilt, the waveform is then truncated.

Further, Brewer et al. in U.S. Pat. No. 5,978,706 teaches a method of continuously determining the truncation point of a damped sinusoidal waveform, similar to that described in the '442 patent, but applied to the delivery of a sinusoidal waveform. The '706 patent discloses a method of truncation that requires measurement of the patient's resistance. Specifically, a pre-calculated design rule to determine truncation time based on patient impedance that is continuously measured and discretely updated during delivery of the waveform is implemented. This method relies on a measurement of impedance prior to shock delivery, rather than a real-time impedance measurement during shock delivery.

Lerman, in U.S. Pat. Nos. 4,574,810, 4,771,781, and 5,088,489 discloses a method of delivering sinusoidal current to transthoracic defibrillation paddles/electrodes and then measuring the resultant voltage across the electrodes. This voltage is then used to determine the patient's transthoracic resistance. The resistance value is then used to scale a subsequent shock by scaling the voltage to which the capacitor is charged prior to shock delivery. The method is equivalent to a current-based process, because the peak current of the waveform becomes the controlling parameter.

Charbonnier, et al, in U.S. Pat. No. 4,328,808, proposes a method of computing transthoracic resistance given a predetermined stored energy and, by measurement of peak output current, to perform computations during delivery of a damped sine waveform. These data are used to determine delivered energy and to trigger an audible alarm if the resistance falls outside a preset boundary. In U.S. Pat. No. 5,111,813, Charbonneier et al. specify an "impedance normalized delivered energy" in lieu of current.

Gliner et al., in U.S. Pat. Nos. 5,593,427, 5,601,612, 5,607,454, 5,620,470, 5,735,879, 5,749,904, 5,749,905, 5,776,166, 5,803,927, 5,836,978, 6,047,212, disclose a method for delivering a truncated exponential waveform to a patient. As the pulse is delivered, the voltage remaining on the storage capacitor is monitored. Under certain circumstances, the waveform or its first phase is truncated when the voltage decays to a certain value. However, if too little or too much time passes, the waveform may be truncated early or late.

Lopin and Avati, in U.S. Pat. Nos. 5,733,310, 5,769,872, 5,797,968, 5,800,462, 5,800,463, 5,904,706, 6,096,063, describe a method of measuring patient resistance by using a "sensing pulse" applied immediately before defibrillator discharge. This pulse is applied as a voltage and the resulting current is then measured and used to compute resistance.

In U.S. Pat. No. 5,201,865, Kuehn discloses a method of measuring lead impedance by measuring the time it takes a capacitor to discharge through a precision resistor and then comparing this time to the time required to discharge the same capacitor through the patient load.

In U.S. Pat. Nos. 5,549,643 and 5,645,573, Kroll and Smith describe a method of timing the duration of a capacitor-discharge truncated exponential waveform defibrillation shock by first waiting for the capacitor voltage to decay by a certain percent. Then it extends the waveform by a fixed duration beyond this percentage.

In a Ph.D. thesis, entitled "A Controlled-Power Arbitrary Waveform Method of Defibrillation" (March 2000, Purdue University), Havel presents a method for instantaneously controlling output power to the load without measuring output current or load resistance. This method uses a pulse width modulator control scheme that uses the voltage on the storage capacitor as a feedback parameter. Thus, output power is controlled by actively calculating the rate of decay of the energy storage capacitor.

In U.S. Pat. No., 5,481,238, issued to Carsten, et al., U.S. Pat. No. 5,629,842, issued to Johnson, et al., and U.S. Pat. No. 5,165,162 issued to Charles, there are descriptions of how compound inductors may be assembled in buck and boost regulators. For example, a toroidal inductor member formed from a plurality of turns of wire is described in the '842 patent, including an inductor with a segmented toroidal core with a winding wound thereon in the '162 patent.

Typically, ICDs have the capability of providing a variety of defibrillation waveforms. In the main, these waveforms have either been monophasic or biphasic waveforms applied as truncated exponential waveform pulses. Clinically, however, there is a need for an apparatus and method that would take account of changes in patient resistance. A patient's impedance changes due to any of a wide variety of causes, therefore the defibrillation waveform pulse may provide far less energy than what the physician has programmed. Thus, among other needs, a need exists for new methods to provide a consistent amount of energy in the presence of varying impedances, as is disclosed in the present invention.

SUMMARY OF THE INVENTION

The present invention provides structures and methods for delivering a complex slow-rise defibrillation waveform specifically, when a predetermined amplitude is reached for an ascending waveform (e.g., a slow-rise, ramp-type waveform), the waveform transitions to an exponential decay portion for a period of time and subsequently, a truncation occurs. In the event that a first complex bi-phasic ramp waveform is implemented, a second opposite polarity waveform may be delivered. The second waveform is preferably of similar shape to the first waveform, but of a less amplitude. The inventors have found that traditional sharp leading-edge defibrillation waveforms, whether mono- and/or bi-phasic, tend not to place as much charge "on the membrane" because the traditional waveforms do not mimic physiologic processes of cardiac tissue (i.e., cardiac myocytes).

A complex waveform in accordance with the present invention comprises a voltage-controlled waveform that is ascending over time, such a wavefrom is commonly termed a "ramp" waveform based on its characteristic shape that display a low or near-zero initial voltage followed by an exponential decay of the waveform. Such a complex waveform may be optionally truncated following the exponential decay portion of the waveform and/or may transition to a reverse polarity waveform having a similar, complex shape. Although voltage-controlled waveforms are described herein, current-controlled embodiments of the present invention are also inherently within the scope of the present disclosure.

As will become clear, the use of alternative complex defibrillation waveforms can improve the defibrillation efficacy of cardiac tissue while providing advantages such as lower defibrillation threshold (DFT), potentially smaller supporting circuitry (e.g., capacitor and battery cells, transformers, etc.), reduced perception of pain by a patient receiving defibrillation therapy. It is believed that these new alternative complex ascending ramp waveforms with single or multiple phases may in general increase the efficiency of putting charge on the cardiac membrane and therefore providing a more physiologically appropriate mode of defibrillating cardiac tissue. The implementation and feasibility of these waveforms using current ICD or AED platforms provides relatively immediate and significant advances not previously known or used in the art.

BRIEF DESCRIPTION OF THE DRAWINGS

FIG. 8 depicts three examples, a single toroid with a magnetic core, a single toroid (no magnetic core), and two stacked toroid, respectively, used to experimentally develop the inductor designs mentioned with respect to FIG. 7.

DETAILED DESCRIPTION OF THE DRAWINGS

Figure 1:
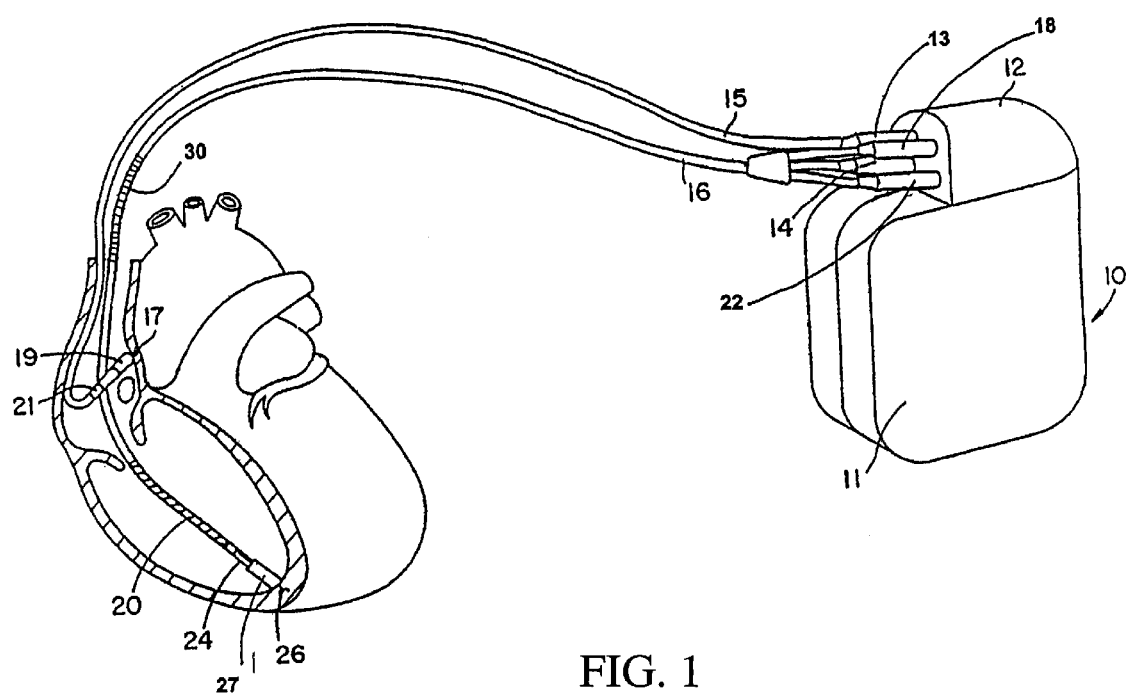
FIG. 1 is an illustration of a ICD type system according to the present invention.

Referring now to FIG. 1, a defibrillation device 10 couples to leads 15, 16 as is known in the art to provide an ICD system according to the present invention. The leads 15, 16 are adapted to electrically couple to a mass of ventricular and/or atrial cardiac tissue and the locations depicted are intended as illustrative, not limited, a different number and/or type of leads may be used according to the present invention. For example, U.S. Pat. Nos. 4,932,407; 5,174,288, and 5,261,400, disclose and depict a variety of devices that may be used according to the present invention and each patent is hereby incorporated by reference herein. For example, a ventricular lead 16 having an extendable helix electrode 26 and a ring electrode 24 coupled to a distal end portion of lead 16, said extendable helix electrode 26 retractably mounted within an insulative head portion 27. Electrodes 24,26 can be used in a bipolar electrical arrangement (e.g., ventricular pacing and sensing evoked and intrinsic ventricular activity), although unipolar electrodes may be employed in lieu of the depicted bipolar electrodes 24,26. In the event that a unipolar electrical arrangement is employed, electrodes 24,26 electrically communicate with a surface portion of the device casing (or canister) 11. As is known, the surface portion of the casing 11 operates as a common or indifferent electrode to complete the electrical pacing, sensing and/or defibrillation circuits of the device 10. Ventricular lead 16 also includes one or more high voltage coil electrodes 20. As applicable, said high voltage coil electrodes 20 are sometimes referred to as a right ventricular (RV) coil or a superior vena cava (SVC) coil, as applicable. The high voltage electrode 20 delivers defibrillation and/or cardioversion stimulation therapeutic pulses to adjacent cardiac tissue. In some embodiments, high voltage coil electrode 20 is mechanically and electrically coupled to the lead 16 so that when the distal tip of lead 16 is disposed proximate a portion of the apex of the RV, coil 20 is positioned in electrical communication with a portion of the myocardial tissue of the RV. A second high voltage coil electrode 20 may be operatively coupled to a single lead 16 (or an additional lead—not depicted), said second high voltage coil electrode 30 operatively coupled to a different portion of myocardial tissue or elsewhere (e.g., in electrical communication with the SVC), and/or positioned in electrical communication with a portion of myocardium via the subclavian vein or one or more cardiac veins (e.g., via the coronary sinus, great vein, or branches thereof). These coil electrodes can be used for endocardial electrogram (EGM) sensing and/or applying cardioversion or defibrillation pulses to the RV or the left ventricle (LV). Lead 16 thus includes respective concentric coil conductors, separated from one another by electrically insulative material such as tubular insulative sheaths and extending the length of the lead 16 for providing electrical communication between the ICD device 10 and respective ones of electrodes 20,24,26,30.

Atrial lead 15 as illustrated includes, located adjacent to the distal end, an extendable helix electrode 17 and a ring electrode, the helix electrode 17 being mounted retractably within an insulative head portion 19 of the atrial lead 15. Electrodes 17,21 are oftentimes configured for bipolar delivery of atrial pacing therapy and/or sensing atrial depolarizations, although electrodes 17,21 may be configured for unipolar bipolar pacing and/or sensing (i.e., with electrical communication to an electrically conductive portion of the canister 11), which portion acts as a common or indifferent electrode as is known in the art. As depicted in FIG. 1, atrial lead 15 is not equipped with one or more coil electrodes for delivery of cardioversion or defibrillation pulses; however, according to the present invention such electrodes may be operatively coupled to atrial lead 15. That is, the system depicted is not meant to preclude inclusion of such electrodes as they may be advantageously employed according to the present invention.

An ICD type device, or defibrillator 10, is shown in combination with atrial and ventricular leads, with the lead connector assembly 13, 14, 18,22 being inserted into the connector block 12 of the device 10. A specific example of a defibrillation pulse generator that may be used in conjunction with the present ventricular lead is disclosed in U.S. Pat. No. 4,953,551. Of course, other types of ICD (and AED)

units can be used. For example, U.S. Pat. Nos. 5,163,427 and 5,188,105 in relevant parts are hereby incorporated by reference herein as representative therapy delivery devices for detecting a cardiac arrhythmia condition and, depending on the type of cardiac arrhythmia condition detected, delivering an appropriate cardioversion and defibrillation therapy according to the present invention. Thus, the present invention should not be viewed as limited to any particular depicted embodiment, but rather should be viewed as applying to every type of medical device that can deliver a therapeutic cardioversion or defibrillation therapy for controlling arrhythmias.

Figure 2:
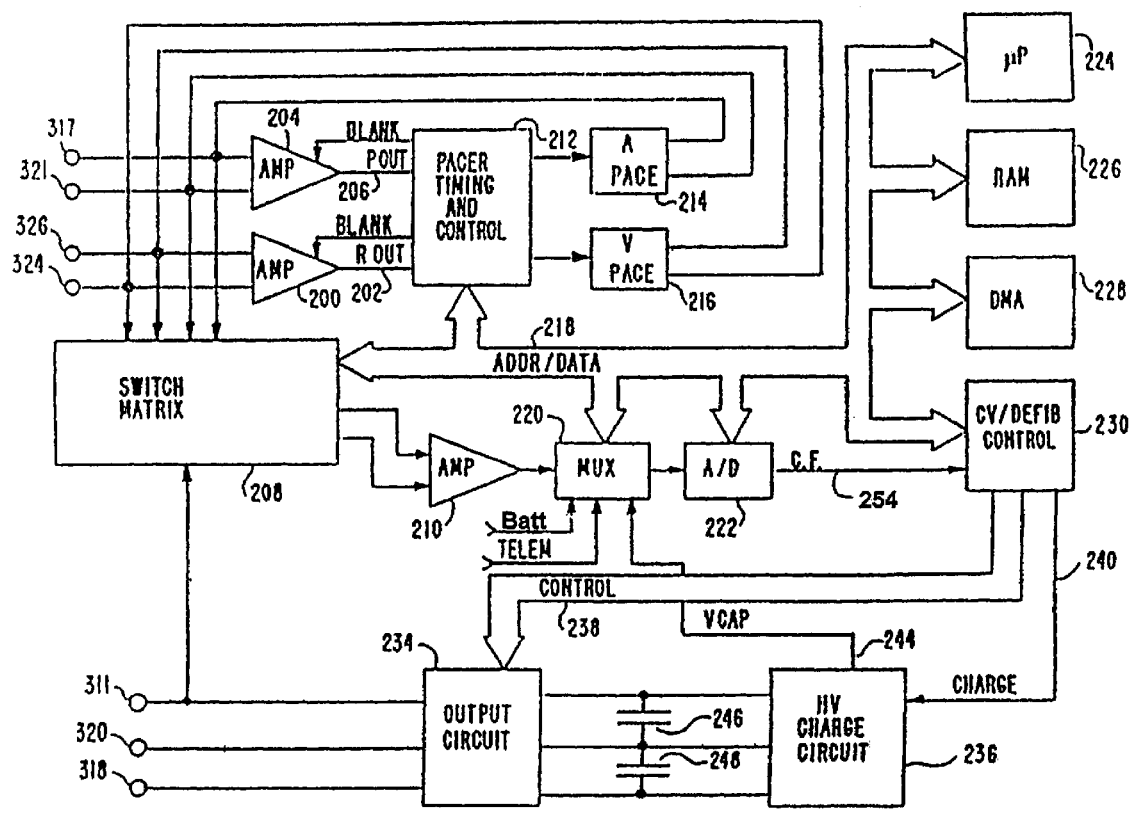
FIG. 2 is a block, functional diagram of an ICD type device adapted to carry out the features of the present invention.

FIG. 2 is a functional schematic diagram of an ICD which may advantageously embody the present invention. This diagram illustrates an exemplary type of device 10 in which the invention may be implemented, although the present invention may be implemented in a wide variety of cardiac therapy delivery devices, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such as nerve stimulation or drug administration. Such devices typically include programmable parameters and executable instructions for performing therapy delivery. The executable instructions are typically stored on one or more types of computer readable media and operate under microprocessor control.

The device 10 is provided with a lead system including electrodes (e.g,. as illustrated in FIG. 1). Alternate lead systems may of course be substituted for those depicted herein. If the electrode configuration of FIG. 1 is employed, the electrodes illustrated in FIG. 2 correspond to those depicted in FIG. 1 as described hereinbelow. Electrode 311 corresponds to electrode 16, and comprises an uninsulated portion of the housing of an ICD. Electrode 320 corresponds to electrode 20 and comprises a defibrillation electrode disposed in electrical communication with a portion of myocardial tissue of the RV. Electrode 318 corresponds to electrode 30 and comprises a defibrillation electrode located in the SVC. Electrodes 324 and 326 correspond to electrodes 24 and 26, and are used for sensing and pacing in a ventricle (the RV or, although not depicted, the LV). Electrodes 317,321 correspond to electrodes 17,21 and are used for pacing and/or sensing atrial depolarizations.

Electrodes 311,318,320 are operatively coupled to a high voltage output circuit 234. Electrodes 324,326 are located on or in the RV and are coupled to the R-wave amplifier 200, which preferably comprises an automatic gain controlled amplifier providing an adjustable sensing threshold as a function of the measured amplitudes of ventricular depolarization wavefronts (R-waves). As is known, a signal is generated on R-out line 202 whenever the signal amplitude sensed between electrodes 324,326 exceeds a present sensing threshold. Said sensing threshold may be programmed to may be dynamically adjusted based on a number of factors.

Electrodes 317,321 are located on or in the atrium and are coupled to a P-wave amplifier 204, which preferably comprises an automatic gain controlled amplifier providing an adjustable sensing threshold as a function of the measured P-wave amplitude. A signal is generated on P-out line 206 whenever the signal sensed between electrodes 317,321 exceeds the present sensing threshold. The general operation of the R-wave and P-wave amplifiers 200,204 may be better understood by reference to U.S. Pat. No. 5,117,824, by Keimel et al., issued 2 Jun. 1992, and entitled, "Apparatus for Monitoring Electrical Physiologic Signals," the contents of which are hereby incorporated herein by reference in its entirety.

Switch matrix 208 is used to select which of the available electrodes are coupled to wide band (0.5–200 Hz) amplifier 210 for use in digital signal analysis. Selection of the discrete electrodes used is controlled by the microprocessor 224 via data/address bus 218, which selection may be varied as desired. Signals from the electrodes selected for coupling to bandpass amplifier 210 are provided to multiplexer 220, and thereafter converted to multi-bit digital signals by A/D converter 222, for storage in random access memory (RAM) 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art (e.g., digital signal processing, analog signal processing, as well as converting signals between digital and analog and then processing same).

The arrhythmia detection method of the ICD may include prior art tachyarrhythmia detection algorithms. As described below, the entire ventricular arrhythmia detection methodology of presently available ICDs employed as part of the arrhythmia detection and classification method may be employed according to the present invention. However, any of the various arrhythmia detection methodologies known to the art can also be usefully employed in alternative embodiments of an ICD or AED. In addition, a remote activation sequence may be used either automatically or manually to invoke therapy delivery according to the present invention.

One embodiment of an appropriate system for delivery and synchronization of ventricular cardioversion and defibrillation pulses and for controlling the timing functions related to them is disclosed in more detail in commonly assigned U.S. Pat. No. 5,188,105 issued to Keimel on 23 Feb. 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Patent Application No. WO92/18198 by Adams et al., published 29 Oct. 1992, and in U.S. Pat. No. 4,316,472 to Mirowski et al., issued 23 Feb. 1982, both of which are hereby incorporated herein by reference.

In the event that cardioversion or defibrillation therapy delivery is required, microprocessor 224 employs an escape interval timer to control the timing of the attendant cardioversion and defibrillation stimulation pulses, as well as refractory periods for the associated cardiac chamber(s). In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246,248 via charging circuit 236, under control of high voltage charging control line 240. The voltage on the high voltage capacitors is monitored via VCAP line 244, which is passed through multiplexer 220 and, in response to reaching a predetermined value set by microprocessor 224, results in generation of a logic signal on Cap Full (CF) line 254, terminating charging. Then, delivery of a complex slow rise ramp waveform begins, terminating with an exponential decay function after a preset time or predetermined amount of energy is delivered from a capacitor. The exponential decay may be derived from the native exponential decay constant of the capacitors or as applied according to a desirable exponential function, and the like. Thereafter, timing of the delivery of the defibrillation or cardioversion pulse is controlled by pacer timing/control circuitry 212. Following delivery of the fibrillation or tachycardia therapy the microprocessor 224 then, operative circuitry of the device 10 optionally reverts to delivery of cardiac pacing therapy (until a next successive interrupt due to pacing or the occurrence of a sensed atrial or ventricular depolarization or arrhythmia).

However, any known cardioversion or defibrillation pulse control circuitry is believed usable in conjunction with the present invention. For example, other circuitry controlling the timing and generation of therapeutic cardioversion and defibrillation therapy may be employed in accordance with the present invention (e.g., as disclosed in U.S. Pat. No. 4,384,585, issued to Zipes on 24 May 1983 or in U.S. Pat. No. 4,949,719 issued to Pless et al., cited above, and in U.S. Pat. No. 4,375,817, issued to Engle et al., each of which is hereby incorporated herein by reference in their entireties).

In the illustrated device 10, delivery of the cardioversion or defibrillation pulses is performed by output circuit 234 operating under control of control circuitry 230 via control bus 238. Output circuit 234 determines whether a monophasic or biphasic pulse is delivered, whether the housing 311 serves as an indifferent cathode or anode and which electrodes are involved in delivery of the therapy.

Figure 3A:
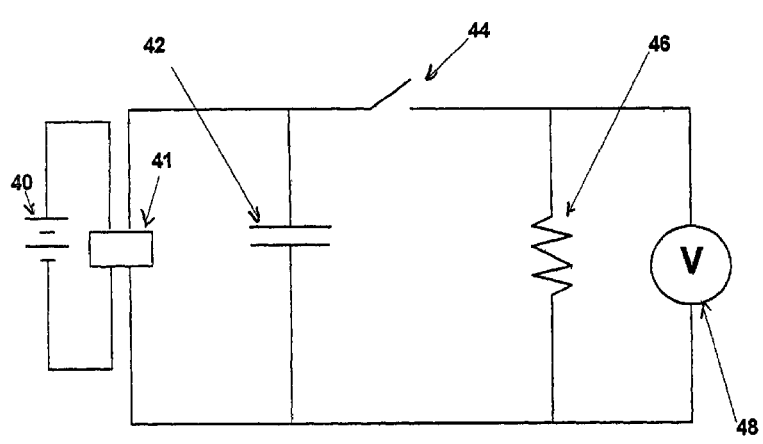
FIG. 3a is a block diagram of the circuit used to generate a truncated exponential waveform used in previous ICDs.
Figure 5:
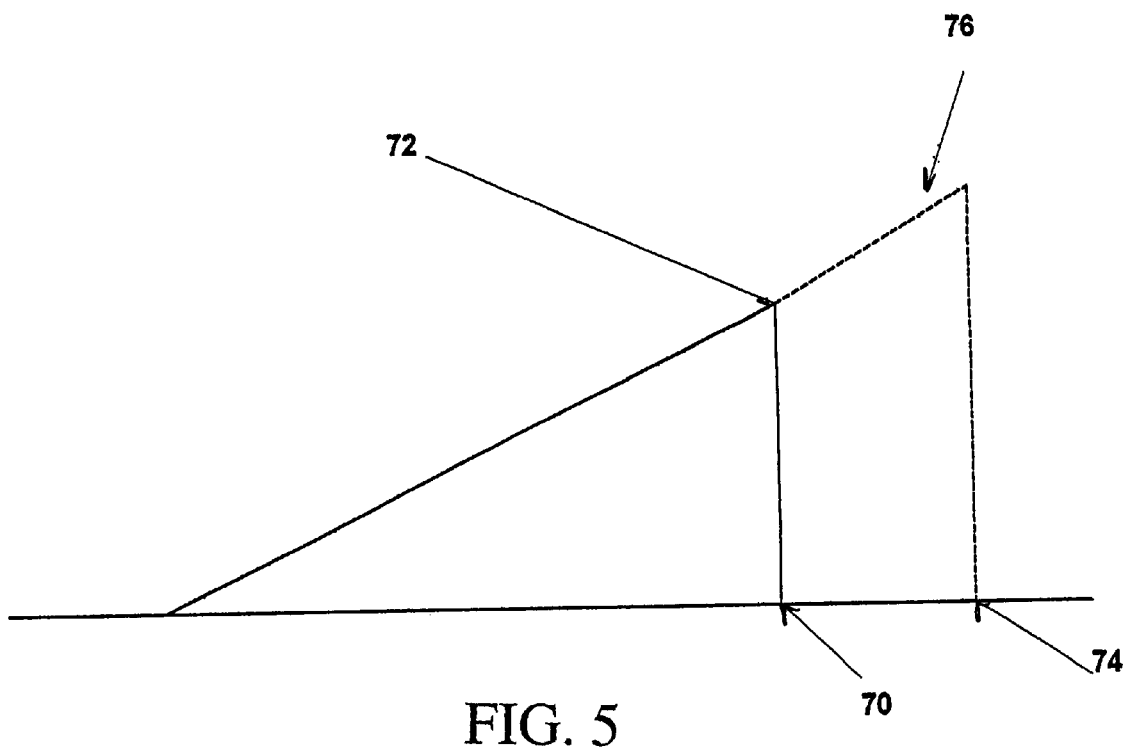
FIG. 5 is an illustration of a simple ramp waveform useful in describing some of the concepts of present invention.

Now referring to FIG. 3A additional detail is provided regarding output circuit 234 for the delivery of a truncated exponential waveform and to FIG. 5 for the delivery of an arbitrary waveform, both of which are the subject of the present invention. An example of output circuitry for delivery of biphasic pulse regimens may be found in the above-cited patent issued to Mehra and in U.S. Pat. No. 4,727,877, hereby incorporated herein by reference.

An example of circuitry which may be used to control delivery of monophasic pulses is set forth in commonly assigned U.S. Pat. No. 5,163,427 issued to Keimel in 17 Nov. 1992, also incorporated herein by reference in its entirety. However, output control circuitry as disclosed in U.S. Pat. No. 4,953,551, issued to Mehra et al. on 4 Sep. 1990 or U.S. Pat. No. 4,800,883, issued to Winstrom on 31 Jan. 1989 both incorporated herein by reference in their entireties, may also be used in conjunction with a device embodying the present invention for delivery of biphasic pulses. On the other hand, circuitry similar to that shown in FIG. 5 of the '883 patent, which is used to generate somewhat arbitrary waveforms, (e.g., ascending ramp and square waveforms, among others) can be employed in conjunction with practicing the present invention.

In the event that fibrillation is identified, the typical therapy will be the delivery of a high amplitude defibrillation pulse, typically in excess of about 25 joules. Lower energy levels may be employed for cardioversion. As in the case of currently available ICDs, and as discussed in the above-cited references, it is envisioned that the amplitude of the defibrillation pulse may be incremented in response to failure of an initial therapeutic pulse or pulses to terminate a fibrillation condition. Prior art patents illustrating such pre-set therapy menus of anti-tachyarrhythmia therapies include the above-cited U.S. Pat. No. 4,830,006, issued to Haluska et al., U.S. Pat. No. 4,727,380, issued to Vollmann et al. and U.S. Pat. No. 4,587,970, issued to Holley et al.

The remainder of the circuitry is dedicated to the provision of cardiac pacing, cardioversion and defibrillation therapies, and, for purposes of the present invention may correspond to circuitry known in the prior art. An exemplary apparatus for accomplishing pacing, cardioversion and defibrillation functions is described and depicted as follows. The pacer timing/control circuitry 212 includes programmable digital counters which control the basic time intervals associated with DDD, VVI, DVI, VDD, AAI, DDI, ADI pacing (all with or without activity sensing capability) and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves will not restart the escape pacing interval timing. The durations of these intervals are determined by microprocessor 224, in response to stored data in memory 226 and are communicated to the pacing circuitry 212 via address/data bus 218. Pacer circuitry 212 also determines the amplitudes and pulse widths of the cardiac pacing pulses under control of microprocessor 224.

During pacing, the escape interval timers within pacer timing/control circuitry 212 are reset upon sensing of R-waves and P-waves as indicated by signals on lines 202,206, and in accordance with the selected mode of pacing on timeout trigger generation of pacing pulses by pacer output circuitry 214,216, which are coupled to electrodes 317,321,324,326. The escape interval timers are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval timers when reset by sensed R-waves and P-waves may be used to measure the durations of intrinsic intervals (e.g., R—R intervals, P—P intervals, P-R intervals, R-P intervals) or monitor evoked intervals (e.g., A-V intervals, V—V intervals, V-A intervals), which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval timers therein. This type of pacing regimen is used to define refractory periods during which detection of R-waves and P-waves is ineffective to restart the escape interval timers. Alternatively, circuitry for controlling the timing and generation of anti-tachycardia pacing pulses as described in U.S. Pat. No. 4,577,633, issued to Berkovits et al. on 25 Mar. 1986; U.S. Pat. No. 4,880,005, issued to Pless et al. on 14 Nov. 1989; U.S. Pat. No. 4,726,380, issued to Vollmann et al. on 23 Feb. 1988; and U.S. Pat. No. 4,587,970, issued to Holley et al. on 13 May 1986, all of which are incorporated herein by reference in their entireties may also be used.

In modern ICDs, the physician, from a menu of therapies that are typically provided, programs the specific therapies into the device. For example, on initial detection of an atrial or ventricular tachycardia, an anti-tachycardia pacing therapy may be selected and delivered to the chamber in which the tachycardia is diagnosed, or to every affected chamber. Following an optional redetection of a potentially lethal tachycardia, a more aggressive anti-tachycardia pacing therapy may be scheduled. If repeated attempts at anti-tachycardia pacing therapies fail, a higher energy cardioversion pulse may be selected for subsequent delivery. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is below a preset threshold. The references cited above in conjunction with descriptions of prior art tachycardia detection and treatment therapies are applicable here as well. Likewise, the amplitude of a defibrillation waveform may be iteratively increased if prior efforts to terminate a potentially lethal cardiac arrhythmia fail.

Figure 3B:
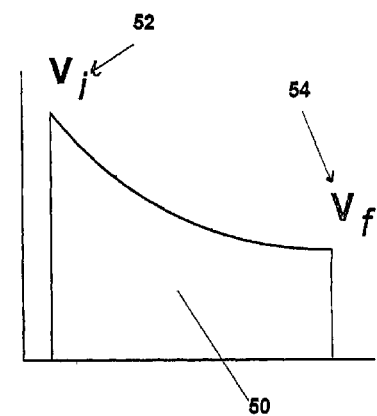
FIG. 3b illustrates a common monophasic truncated exponential waveform.

Referring to FIGS. 3A and 3B, those familiar with the art will recognize that the type of circuit described in FIG. 3A is used to generate traditional, simple monophasic, truncated exponential waveform 50 in FIG. 3B. With reference to FIG. 3A, ICD battery 40 provides voltage to capacitor charging circuit 41 which delivers energy to capacitor 42. At the start of the formation of defibrillation waveform, switch 44 closes and a voltage is delivered across patient/resistance 46. In this embodiment, voltage as measured by voltage meter (V) 48 with a trend line defined by $V_i$ 52 and then decays down to $V_f$ 54 as illustrated in FIG. 3B. At some point into the waveform, switch 44 re-opens. Thus, truncating the waveform at $V_f$ 54.

The method is presented to illustrate a common prior art technique used to truncate a simple exponential decay waveform 50 when voltage $(V_f)$ 54 of waveform 50 reaches a certain level. With respect to the present invention, this illustration can be viewed with reference to the decay portion of a desirable complex slow-rise waveform, after the amplitude of said complex waveform reaches a desired threshold amplitude. As is understood by those skilled in the art, the voltage of waveform 50 is proportional to the delivered energy. As the voltage decays from initial voltage $(V_i)$ 52 to final voltage $(V_f)$ 54, equation 1 defines the delivered energy in relation to the voltage left on the capacitor at the beginning of waveform 50.

$$U_i = \tfrac{1}{2} C V_i^2 \quad \text{(Equation 1)}$$

where U=energy, C=capacitance, and V=voltage.

Specifically, Equation 2 defines the energy in relation to $V_f$ 54:

$$U_f = \tfrac{1}{2} C V_f^2 \quad \text{(Equation 2)}$$

where U=energy, C=capacitance, and V=voltage.

As mentioned, the voltage increases at $V_i$ and decreases down to $V_f$. Specifically, when switch 44 opens the waveform is truncated. One aspect of the present invention is determining the point at which the waveform should be truncated. The waveform is truncated by determining the remaining energy on capacitor 42. Algorithmically, the difference between $U_i$ and $U_f$ yields its magnitude of deliverable energy at any given initial and final voltages. Accordingly, the ICD would deliver the required energy to the load so long as the energy is truncated at the proper final voltage in the waveform. When the voltage on voltage meter 48 reaches the desired final voltage, the switch opens to truncate the waveform.

Another aspect of the invention relates to the tilt of the exponential decay portion of a complex slow-rise defibrillation waveform. In general, tilt is defined as the percentage by which the voltage decays over the course of the waveform. In a fixed tilt method, the tilt percentage is kept fixed regardless of the load. This would mean in a higher impedance patient, it might take longer to discharge the capacitor, but the waveform is still truncated at the same point. Of course, the slow rise, or ramp, portion as well as the decay portion of the diverse complex waveforms according to the present invention may have a variety of magnitudes; however, a tilt of between approximately 45% to about 75% may be used in accordance with some forms of the present invention.

In any event, a physician merely needs to program the desired energy (in joules) to be delivered from a complex slow-rise waveform commensurate with the programmed value.

However, when the output voltage or current of the ICD is actively controlled during delivery of a complex slow rise waveform according to the present invention, a new problem potentially arises. That is, the total delivered energy becomes dependent on the (periodically modulating) load resistance, or impedance, of myocardial and other thoracic tissue of a patient. Since the ICD pre-stores usable energy on a capacitor, two scenarios, inter alia, can arise that depend on such modulating load resistance. First, there may not be enough stored energy to deliver a desired waveform. Alternatively, there may be an excess of usable energy on the storage capacitor after the waveform has been delivered. The first case results in a waveform that is likely distorted or cut off, while, in the latter case, energy with the potential to further improve the defibrillation success rate is wasted.

Preferably, a consistent, desirable and predetermined amount of defibrillation energy is delivered to the patient regardless of the changing load in an individual patient or the changing load that one finds clinically from patient to patient. This consistency allows an ICD with active control of the output waveform to use as much stored energy as possible when delivering a waveform according to the present invention. When a physician programs the amount of energy (in joules) that need to be delivered during cardioversion or defibrillation therapy, the physician should be assured that this amount of energy is being delivered, no matter what the actual load impedance is within the patient. The circuitry depicted is designed primarily to ensure that the energy programmed is delivered, regardless of the changing patient load.

Figure 4:
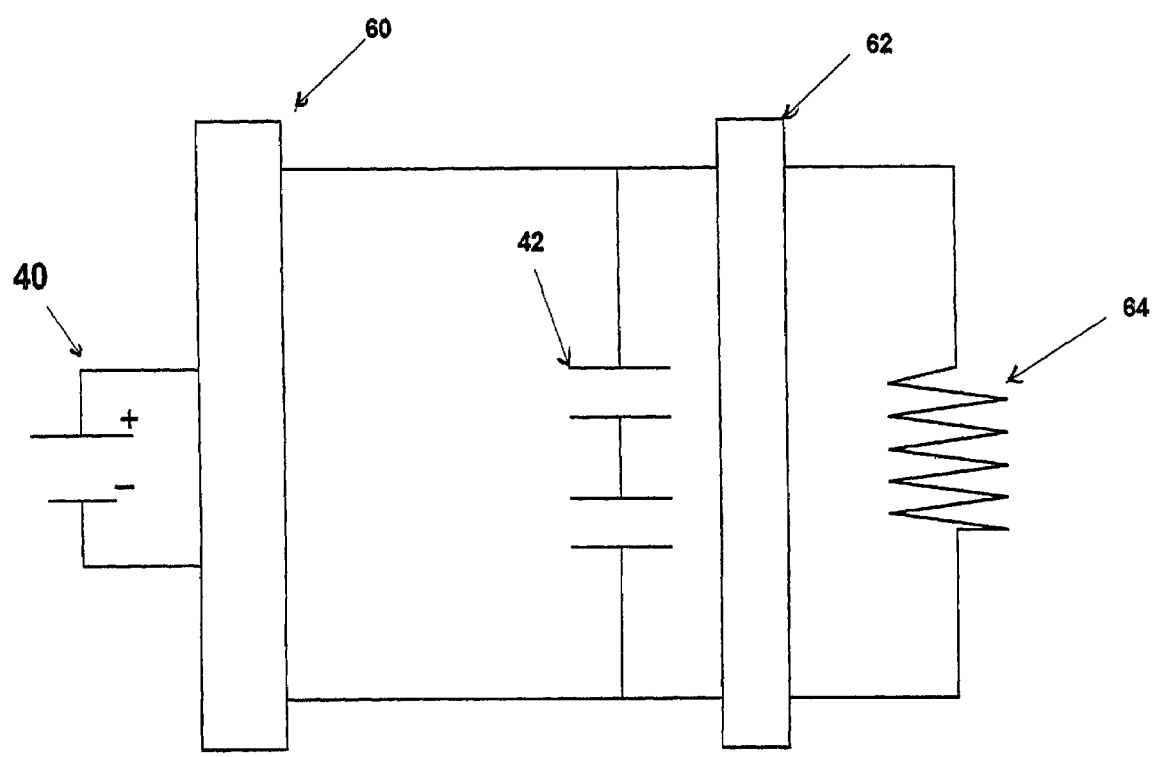
FIG. 4 is a block diagram of the circuit used to generate arbitrary waveforms of the present invention.
Figure 6:
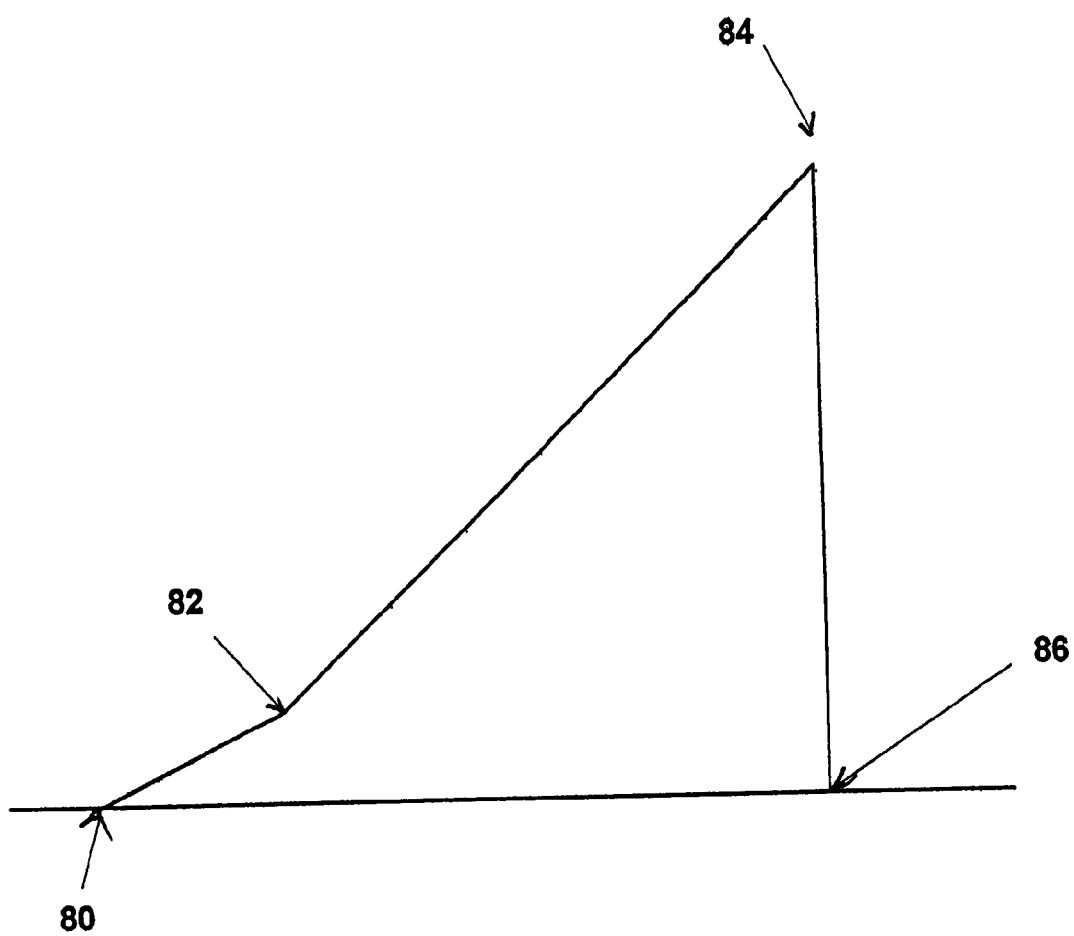
FIG. 6 is an illustration of a ramp waveform also useful in describing some of the concepts of the present invention.

FIG. 4 is a block diagram of the circuit implemented to generate arbitrary waveforms such as the complex slow-rise defibrillation waveforms of the present invention. However, said circuit may benefit from one or more programmable logic devices in order to best implement the complex waveforms, as use of such devices is known in the art. An ICD battery 40 delivers energy to charging transformer 60 that in turn conveys energy to capacitor 42. At the start of the formation of defibrillation waveform, switching power converter 62 transforms the energy stored in capacitor 42 into any arbitrary waveform shape, but preferably into a complex slow-rise waveform of the type described herein (e.g., and as depicted in FIG. 5 and FIG. 6), regardless of patient resistance or impedance load 64.

The switching power converter 62 (see FIG. 7 for details) allows the device to step down the voltage of the output, as well as transform the energy stored in capacitor 42 into the desirable complex slow-rise waveform shape. The amount of energy available at the start is the only constraint. The ICD cannot generate more energy, but in accordance with the present invention, the way the energy is delivered, or the waveform shape, can be tailored to meet various requirements. Thus, the issue of changing impedance/load is successfully addressed by the present invention in that the circuit can deliver any waveform shape to the load, and thus deliver consistent energy, irrespective of load impedance.

Current ICDs defibrillate with more energy than generally needed. A useful goal is to use less delivered energy and/or use the available energy more efficiently. If this is attainable, then an ICD so equipped will achieve the same results with a lower joule output. Current systems achieve their results with truncated exponential waveforms, either monophasic or biphasic. The Huang study, previously mentioned, cites a simple ramp waveform as one distinct possibility that helps reduce the amount of energy required and, according to the inventors of the present invention, the complex slow-rise waveforms taught herein provide particular advantageous benefits such as reduced defibrillation energy requirements, lower DFT, reduced perception of pain during and following defibrillation therapy, and smaller component size, among others.

FIG. 5 is an illustration of a simple truncated ramp waveform used primarily to describe a desirable waveform delivery technique usable in conjunction with the complex slow-rise waveforms of the present invention. For the complex slow-rise waveforms of the present invention, the voltage on the storage capacitor is preferably monitored as the waveform is delivered. Accordingly, the capacitor is precharged to a predetermined voltage and thereby stores a desired amount of energy for delivery of the waveform. Switching power converter 62 (FIG. 4) delivers energy from the capacitor to the patient either by controlling the delivered current or the delivered voltage. A desirable complex slow-rise waveform is a voltage-controlled waveform that increases gradually over time, somewhat similar to the ramp waveform depicted in FIG. 5. Of course, a current-controlled complex waveform may be implemented in accordance with the present invention. The complex slow-rise waveform could be controlled with a constant slew rate, in order to allow both pulse width and peak amplitude to compensate for load variation. When the energy converter has consumed a specific amount of energy during the delivery of the complex waveform determined by the voltage on the capacitor decaying to a certain value, the waveform (or a section thereof), is truncated in the case of multi-phasic or multi-segmented waveforms. With this waveform, a patient with a larger load impedance will receive a longer waveform 70 to 74, with higher peak voltage 72 to 76. As noted above, in lieu of a voltage-controlled waveform as shown in FIG. 5, a current-controlled complex slow-rise waveform could be used (not shown). Whether it is voltage- or current-controlled, the result will still be a consistent amount of total energy delivered to the load irrespective of the patient load impedance. As discussed in more detail below with reference to FIG. 4, setting the gradient or rise rate of the ascending waveform and adjusting the charge voltage of the storage capacitor and the storage capacitor voltage at which the complex waveform transitions from the slow-rise portion to an exponential decaying portion prior to being truncated brings about scaling of either a voltage- or current-controlled waveform to allow the operator to select the desired energy to be delivered. Accordingly, in a desirable delivery technique, the energy switching converter measures the capacitor voltage without converting it into impedance. Then a natural exponential decay of the capacitor occurs (or a predetermined exponential decay function is applied) prior to truncation of the complex waveform as more fully described and illustrated herein.

FIG. 6 is an illustration of another relatively simple ramp waveform useful for describing a family of complex slow-rise waveforms of the present invention. In this illustrated embodiment, the device measures the resistance over the time it takes to deliver a small portion of energy 80 to 82. This results in finding the length of time it takes for the capacitor voltage to decay by a certain percentage. For example, the device could wait to see how long it takes to consume one joule of energy from the capacitor. Then, knowing the voltage of the output waveform for this amount of time, the device can compute in real time the resistance based on equations 3 and 4. Based on this analysis, the energy converter knows how long to extend the pulse 82 to 84 to deliver the programmed level of energy (joules) irrespective of load impedance. One aspect of the present invention is the method of monitoring the delivered energy as a function of time during the first part of the waveform and then using that information to compute the resistance. Once the impedance of the patient is known, the amplitude of the remainder of the waveform is scaled so that the amount of energy delivered by the waveform is consistent. Thus, in FIG. 6, the device delivers a voltage that rises at a certain rate during the first portion of the ramp wave 80 to 82—it is during this portion of the ramp that the device computes the resistance. Then, if the impedance is relatively high, the voltage will rise at a faster rate 82 to 84 than if the resistance is low. In either case, the invention enables the delivery of a consistent amount of energy to a varying load and/or unknown load. One of the beneficial implementations of the present invention relates to changes in implanted devices and patient resistance that occurs over time. For example, a lead and/or an electrode coupled to the lead may exhibit changes in load or voltage based on age and other factors and the patient's impedance may vary over time. In the face of these variations, the illustrated techniques enable the delivered energy output to remain consistent with the desirable energy output.

Nevertheless, for background reference and in general, the energy switching converter measures resistance during the waveform by first measuring the length of time d during the waveform that the storage capacitor decays by a certain voltage. This percentage of voltage is used to calculate the delivered energy, $U_f$, to determine a comparator circuit sends a trigger signal when the storage capacitor decays to a certain threshold with a counter circuit keeping track of the elapsed time which is d. If the switching energy converter controls output voltage, the resistance is computed according to the following equation:

$$R = \frac{\int_o^d V^2(t)\,dt}{\gamma U_t} \quad \text{(Equation 3)}$$

where γ is the efficiency of the energy converter, d is the duration required for an energy of $U_t$ to be drawn from the storage capacitor and V(t) is the voltage of the waveform, known before therapeutic delivery of a defibrillation or cardioversion therapy with a controlled voltage output.

If the switching energy converter controls output current and uses the same method, the resistance is computed according to the following equation:

$$R = \frac{\gamma U_t}{\int_o^d I^2(t)\,dt} \quad \text{(Equation 4)}$$

where I(t) is the current of the delivered waveform. Once the resistance of the patient is known, the amplitude of the remainder of the delivered waveform is calculated so that the amount of energy delivered by the waveform is consistent with the energy of the storage capacitor. In this embodiment and, whether voltage or current are delivered, the switching energy converter measures the impedance during the initial position of the waveform and then scales the amplitude of the remainder of the waveform.

Figure 7:
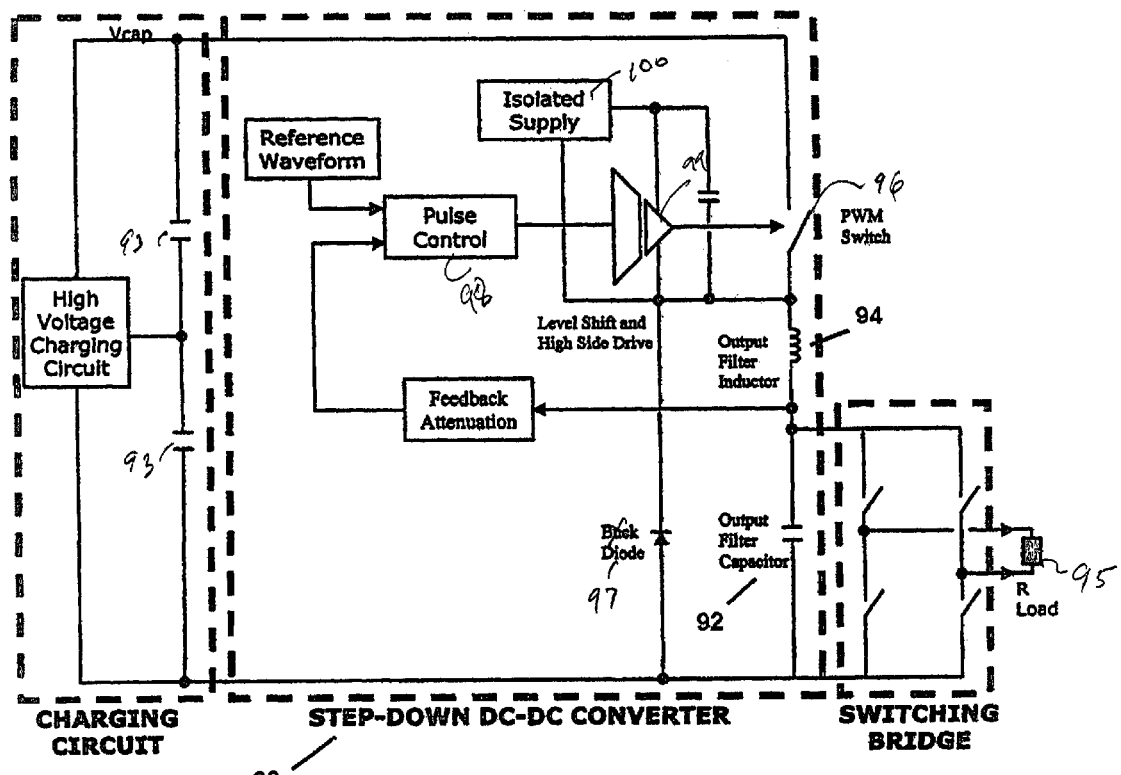
FIG. 7 is a block diagram of the switching power converter preferably used to implement the complex, slow-rise defibrillation waveforms of the present invention.

Referring now to FIG. 7, we next focus implementation of the arbitrary waveforms via a switching energy converter. High frequency switching converters employed in switch-mode power conversion are very useful in this particular application. In a switching converter, the power transistor is used in a switching mode rather than in the continuous mode employed in a linear supply. Switch mode power converters can be configured in their simplest form as a step-down (buck), step-up (boost), or combination buck-boost.

A buck or step-down converter is a power conversion circuit commonly used in dc-to-dc conversion applications in many industries. Descriptions of such circuits may be found in many texts, including, for example, in *Power Electronics: Converters, Applications and Design*, Mohan, Undeland and Robbins, John Wiley & Sons, New York. In this application, the electrical requirements include high efficiency and small component size to minimize the impact of the circuit on overall system size. The buck configuration is suited for implementation with the present invention as compared to the boost and buck-boost converters. It has the least demands on the inductor relative to the other two designs.

The converter is shown in one embodiment in FIG. 7. In this implementation, a dc source voltage is maintained on a plurality of hold capacitors 93. The step-down converter uses the dc voltage as a power source. Within the step-down converter a pulse width modulating switch 96 drives an inductor/capacitor filter into a resistive load 95, as is typical in a buck converter, when the switch 96 is closed, current is sourced from the hold capacitor 93 with current increase controlled by the inductor 94 value. When switch 96 is open, the current continues to flow in the inductor 94 and load, forward biasing the diode 97. The control circuit compares the output voltage to a reference waveform and modifies the duty cycle as required to maintain a specific output voltage. The pulse control circuit 98 drives the modulating switch 96 through a level shift and high side drive circuit. In the implementation shown, this is realized with an opto-driver 99. In other embodiments, this might be accomplished with an isolation transformer or a high voltage semiconductor device used for isolation, along with drive circuit components. The reference waveform can be provided by an analog reference or in a digitized form and converted by a D/A converter. The control circuit as shown is implemented in an analog format with an error amplifier and pulse width modulation comparator. In another embodiment, it might be implemented with a digital controller. In the implementation shown, the error amplifier has a high dc gain for linearity as well as a low pass pole for control loop stability. Control circuitry (not shown) is required to monitor the voltage on the hold capacitor 93 to determine the point at which the desired amount of energy has been delivered for a given phase and the therapy pulse phase change should occur. This hold capacitor 93 monitor can also be used to determine the point at which the final phase should be terminated. Implementation of the switch could be done with a high voltage BIMOSFET, FET, IGBT, or other switch technology. In a desirable embodiment, the switch is implemented with a high current BIMOSFET switching at 500 kHz. The output filter capacitor 92 is a typical surface mounted, high voltage capacitor. The diode 97 requires high reverse voltage blocking capability due to applied voltages in the range of 1000 V. It also requires fast recovery characteristics to reduce switching losses. The diode 97 function could also be implemented with a semiconductor switch along with control circuitry to enable it when the switch 96 is off. Design as a synchronous or resonant converter would include such a switch in lieu of diode 97. The isolated supply 100 could be implemented with an isolation transformer, pulse transformer, or bootstrap supply pump.

The switch frequency, peak inductor current, and output ripple voltage define the requirements for the inductor. In a desirable embodiment, inductor 94 is a 0.5 cc stack of two high flux powder cores (torroids) with common winding to provide an inductance of approximately 14:MH with a common 9:MH at the 40 Amp peak inductor current. Other materials might be used in inductor 94 as well. The therapy pulse period and duty cycle are low enough that heating effects do not enter into the inductor design requirements. In order to minimize volume and limit the inductance change at 40 Amps, a core permeability as low as possible (14, for example) is necessary.

Implementation of such a converter requires output filtering, and inductor 94 is implanted to provide such a filter. To minimize the impact on the size of the ICD, the size of the inductor must be kept small. Minimizing the inductance value contributes to the overall size reduction. Parameter constraints in the converter design limit the minimum value of the inductance. Beyond this, physical design techniques must be used to reduce the physical size, while still meeting electrical design constraints.

A high voltage buck (step-down) converter 90 may be used in an arbitrary defibrillation waveform generator in an ICD device for implementing the desirable complex, slow-rise defibrillation waveforms according to the present invention. Implementation of such a converter requires output filter capacitor 92 that includes inductor 94. To minimize the impact on the size of the implanted device, the physical size of the inductor 94 must be space-volume efficient. Parameter constraints in the converter design will limit the minimum value of inductor 94. Further, physical design techniques must be used to minimize the physical size, while still meeting the electrical design constraints. Inductor electrical constraints for an implanted ICD waveform include tolerance of a significant DC current, 30 amps, for a short duration, less than about 20 ms, with ripple currents of ±10 Amps. Total peak current could therefore be 40 Amps. Heating effects are not significant since the pulse duty cycle is very low. Tolerance of such a current with minimal loss of inductance requires the use of a material such as low permeability high flux powder cores. This material allows significant levels in DC bias while preventing core saturation. Building a magnetic bias into the core could also be used to prevent core saturation.

FIG. 8 depicts three examples, a single toroid with a magnetic core, a single toroid (no magnetic core), and two stacked toroid, respectively, used to experimentally develop the inductor designs mentioned with respect to FIG. 7. The inductance for this converter implementation must be in the range of 10–20:H. A reasonable inductor size to minimize impact to overall device volume is 0.5 cc. The trade-off of low permeability material involves a lower value of inductance per turn of winding. To further optimize the packaging efficiency of the core, a stack of toroid cores with a common winding could be implemented. For a given core, a stack of cores can provide the same inductance with fewer turns that reduces the DC bias effect. The core size can be smaller in diameter with a longer length of stacked cores. This results in a minor improvement in inductor volume for a given inductance value at the specified peak current, as well as a more packaging-efficient aspect ratio. Finally the inductor must not saturate in the presence of externally applied DC magnetic fields less than 1600 Gauss. The distributed air gap of the powder core is ideal for this requirement.

Inductor electrical constraints for a defibrillation waveform include tolerance of a significant DC current (30 Amps) for a short duration pulse (<20 ms) with ripple currents of ±10 Amps. Total peak current could, therefore, be 40 Amps. Heating effects are not significant since the pulse duty cycle is very low. Tolerance of such a current with minimal loss of inductance requires the use of a material such as low permeability, high-flux powder cores. This material allows significant levels in DC bias while preventing core saturation. The inductance for this converter implementation must be in the range if 10–20H. A reasonable inductor size to minimize impact to overall device volume is 0.5 cc. The trade-off of low permeability material is a lower value of inductance per turn of winding. To further optimize the packaging efficiency of the core, a stack of toroid cores with a common winding can be implemented. For a given core, a stack of cores can provide the same inductance with fewer turns, which reduces DC bias effects. The core size can be smaller in diameter with a longer length of stacked cores. This results in an improvement in inductor volume for a given inductance value at the specified peak current, as well as a more packaging-efficient aspect ratio. Finally, the inductor must not saturate in the presence of externally applied DC magnetic fields less than 1600 Gauss. The distributed air gap of the power core is ideal for this requirement.

For example, the material required to design a 14H inductor for 40 Amps of peak current with a volume near 0.5 cc may be sized according to the following formula:

$$N=1000\times[L/(s\times A_l)]^{0.5}$$

$$H=(0.4*Pl*N*Ip)/Ie$$

Where: N=number of turns
L=inductance
s=number of stacked toroids
$A_L$=core inductance (:H) per turn squared
H=magnetizing force (in Oersteds)
Ip=peak current
Ie=core magnetic path length
Volume=Pl(dia/2)$^2$*ht Minimum wire gauge assumed to be 29 AWG. Adiabatic wire heating calculations show this to be reasonable for copper.

The measurement of inductor 94 (in FIG. 8) using example 3 as implemented with 23 turns is:

| L @ 100 kHz | RDC @ 100 kHz |
|---|---|
| 13.8:H | 250 Ohms |

Figure 9:
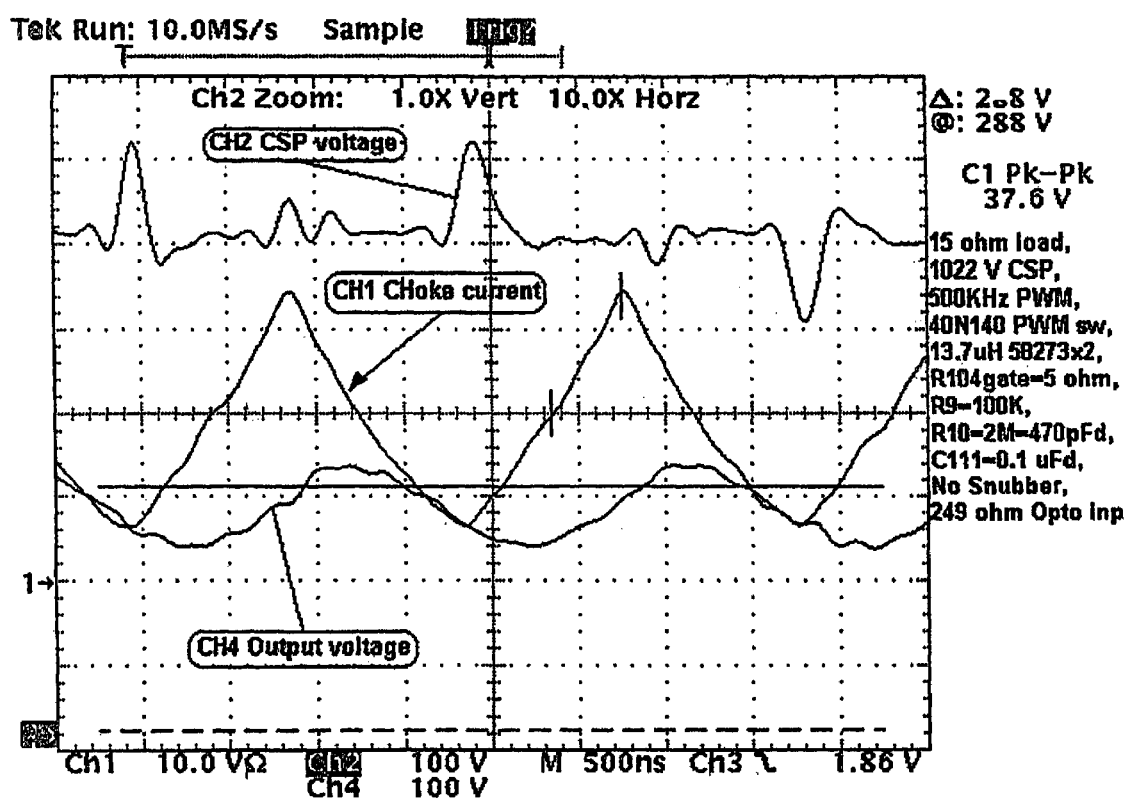
FIG. 9 displays the inductor current in the application at a switching frequency of 500 kHz.

FIG. 9 illustrates the inductor current in the application at a switching frequency of 500 kHz. In FIG. 9, peak inductor current is about 35 Amps (labeled "CH1 Choke Current") with no significant change in current slope. This, and other testing, indicates a stable inductance value over the entire current range. Inductance is calculated as (Vcsp–Vout)* (time change/current change. So, the value of inductance in this case is: L=(580–240)*(400 nS/14A)=9.7:H This indicates that the inductor is performing consistent with the calculations shown hereinabove. No peaking of the waveform was observed, indicating there was no tendency to saturate at this current level. Further testing in the presence of a DC magnetic field resulted in no significant change.

Figure 10:
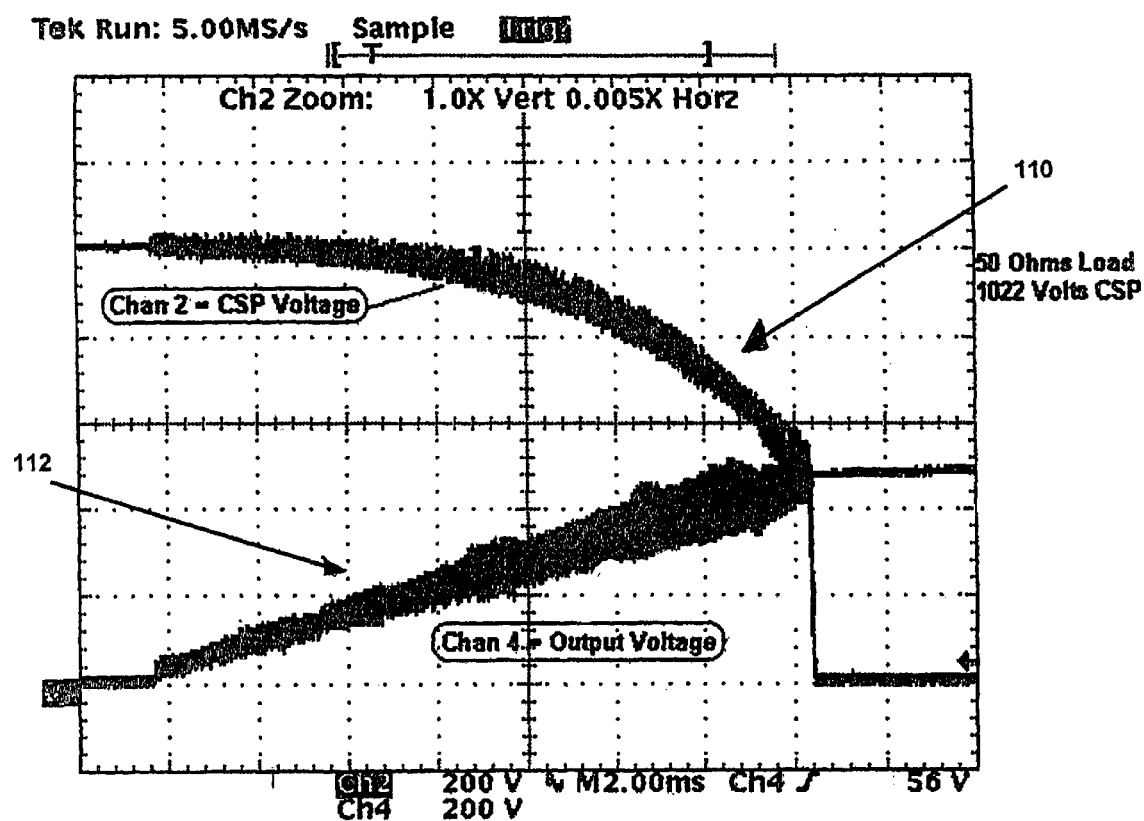
FIG. 10 is an illustration of the delivery of a voltage discharge into a 50-ohm load with a resultant ascending, ramp waveform.

FIG. 10 is an oscilloscope tracing of the delivery of a voltage discharge into a 50-ohm load with a resultant ascending, ramp waveform 112. FIG. 10 illustrates that the CSP voltage 110 applied to a load, consistent with the present invention, results in an ascending, ramp waveform 112, as depicted in this oscilloscope tracing.

Figure 11:
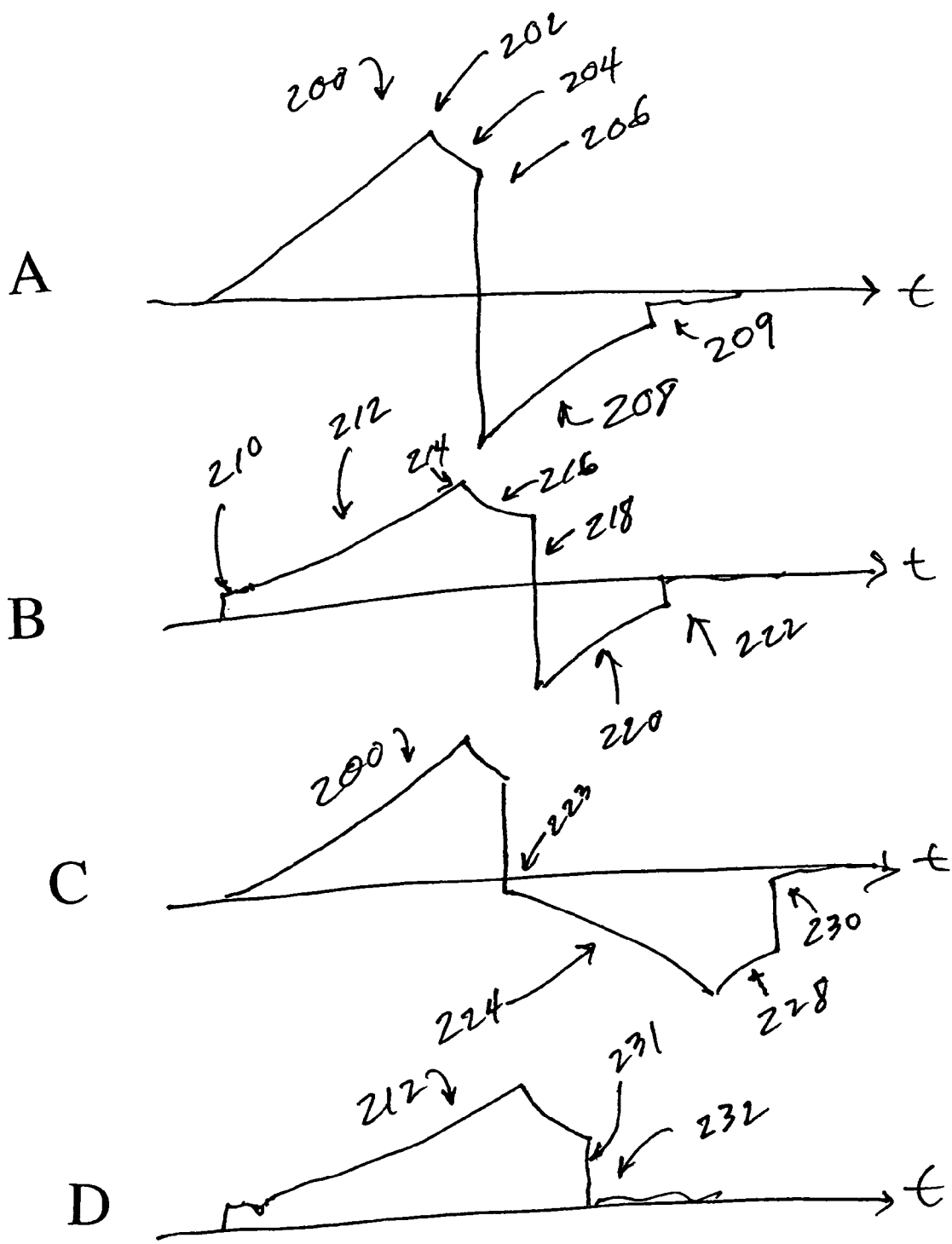
FIGS. 11A–D each depict a complex slow-rise defibrillation or cardioversion waveform according to the present invention.

FIGS. 11A–D each depict a complex slow-rise defibrillation or cardioversion waveform according to the present invention. In FIG. 11A a simple ascending ramp-type waveform 200 that increases in magnitude until the magnitude reaches a peak 202. At the time the waveform 200 reaches the peak 202, an exponential-type decay occurs at 204 (e.g., according to the characteristic decay of a capacitor circuit) until the waveform 200 is truncated at 206. In FIG. 11A a reverse polarity waveform is then generated as is known in the art (at 208). As depicted the portion of the waveform depicted at 208 decays to a nominal value and may be optionally truncated or allowed to continue to decay asymptotically toward a null charge value (at 209).

FIG. 11B depicts another relatively simple ascending ramp-type waveform 212 that increases in magnitude from an initial step function charge level (at 210) until the magnitude reaches a peak 214. At the time the waveform 212 reaches the peak 214, an exponential-type decay occurs at 216 (e.g., according to the characteristic decay of a capacitor circuit) until the waveform 212 is truncated at 218. In FIG. 11B a reverse polarity waveform is then generated as is known in the art (at 208). As depicted, the portion of the waveform depicted at 220 decays to a nominal value before being truncated at 222 before decaying asymptotically toward a null charge value.

FIG. 11C a simple ascending ramp-type waveform 200 (as depicted in FIG. 11A); however, after being truncated (at 223) a reverse polarity ascending-type waveform 224 is then generated with substantially the identical shape as the waveform 200. The waveform 224 rises to a desired magnitude before decaying (at 228) and then being truncated (at 230) to a nominal null value.

In FIG. 11D an ascending ramp-type waveform increases in magnitude from an initial step function (similar to waveform 212 of FIG. 11B) until the magnitude reaches a peak and is truncated at 231 to essentially a null or nominal value or, optionally, allowed to continue to decay asymptotically toward a null charge value (at 232).

The following examples are intended as illustrative of just a few embodiments of the present invention and are not intended to limit the breadth and scope of the invention taught, described, illustrated and claimed herein.

EXAMPLE #1

A system for generating a slow-rise waveform to deliver defibrillation energy to terminate a cardiac fibrillation condition, the system comprising:

means for generating a slow-rise waveform to a predetermined amplitude;

means for converting the slow-rise waveform to an exponential decaying waveform either when the waveform reaches a preset amplitude or for a predetermined period of time; and means for truncating said slow-rise waveform after expiration of said predetermined period of time or after the waveform reaches a preset amplitude.

EXAMPLE #2

A system according to example 1, wherein said slow-rise waveform is a one of the following:

a ramp-up waveform wherein V=mt, an exponential rise waveform wherein V=exp(t/tau), an exponential approach waveform wherein V=1−exp(−t/tau); and wherein said means for generating said slow-rise waveform comprises a switching power converter in electrical communication with at least one storage capacitor cell.

EXAMPLE #3

A system according to example 2, wherein said exponential decaying waveform is truncated to a nominal voltage at the expiration of the predetermined period of time.

EXAMPLE #4

A system according to example 3, further comprising a second waveform having polarity opposite to the slow-rise waveform and means for transitioning from said slow-rise waveform to said second waveform at a predetermined time.

EXAMPLE #5

A system according to example 1, wherein said means for generating the slow-rise waveform includes a pulse-modulating circuit.

EXAMPLE #6

A system according to example 1, wherein said means for generating a slow-rise waveform to an predetermined amplitude includes an initial, relatively low amplitude step function forming a base from which the slow-rise waveform proceeds.

EXAMPLE #7

A system according to example 4, wherein the second waveform is a lower amplitude slow-rise waveform.

EXAMPLE #8

A system according to claim 1, further comprising at least pair of defibrillation electrode assemblies electrically coupled to the system at a proximal end and electrically coupled to a portion of cardiac tissue near a distal end portion and wherein said pair of assemblies includes at least one of the following: a percutaneous electrode, a subcutaneous electrode, an epicardial electrode, an endocardial electrode, a pericardial electrode, a transcutaneous electrode, a surface electrode, a canister electrode, a coil electrode, a ring electrode.

EXAMPLE #9

A method of delivering at least one complex defibrillation waveform to a portion of cardiac tissue, comprising the steps:

confirming the presence of a cardiac arrhythmia terminable by delivery of a defibrillation waveform;

generating at least one pulse-modulated slow-rise defibrillation waveform portion until said slow-rise defibrillation waveform portion reaches a predetermined amplitude;

allowing the amplitude of the defibrillation waveform to decay exponentially for either a predefined period of time or until a predetermined voltage threshold is reached;

truncating said defibrillation waveform; and providing said defibrillation waveform to a portion of cardiac tissue.

EXAMPLE #10

A method according to example 9, further comprising the steps:

after the truncating step, generating a second defibrillation waveform of opposite polarity to said at least one pulse-modulated slow-rise defibrillation waveform; and providing said second defibrillation waveform to the portion of cardiac tissue.

EXAMPLE #11

A method according to example 10, further comprising the steps of determining whether the cardiac arrhythmia has terminated, and if not, repeating the steps of claim 15 at a higher magnitude predetermined amplitude.

EXAMPLE #12

A method according to any of the foregoing examples, wherein a total duration of said defibrillation waveform is in the range of approximately 13 ms to approximately 28 ms.

EXAMPLE #13

A method according to any of the foregoing examples, wherein the method, if applicable, is performed by a system selected from the following list:

an automatic external defibrillator, an implantable medical device, an implantable-cardioverter defibrillator, a pacemaker and/or wherein said method is applied following a positive detection of a potentially lethal arrhythmia and at least one low voltage therapy intended to terminate said potentially lethal arrhythmia.

The preceding specific embodiments and examples are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. A system for generating a slow-rise waveform to deliver defibrillation energy to terminate a cardiac fibrillation condition, the comprising:
    means for generating a slow-rise waveform to an predetermined amplitude;
    means for converting the slow-rise waveform to an exponential decaying waveform for a predetermined period of time; and
    means for truncating said slow-rise waveform upon the expiration of the predetermined period of time, wherein said means for generating a slow-rise waveform to an predetermined amplitude includes an initial, relatively low amplitude step function from which the slow-rise waveform proceeds.

2. A system according to claim 1, wherein said slow-rise waveform comprises a one of the following:
    a ramp-up waveform V, wherein V=mt,
    an exponential rise waveform V, wherein V=exp(t/tau),
    an exponential approach waveform V, wherein V=1−exp(−t/tau); and
    wherein said means for generating said slow-rise waveform comprises a switching power converter in operable electrical communication with at least one storage capacitor cell.

3. A system according to claim 2, wherein said exponential decaying waveform is truncated to a nominal voltage at a predetermined time.

4. A system according to claim 3, further comprising a second waveform having polarity opposite to the slow-rise waveform and means for transitioning from said slow-rise waveform to said second waveform at a predetermined time.

5. A system according to claim 4, wherein the second waveform comprises a lower amplitude slow-rise waveform.

6. A system according to claim 4, wherein said slow-rise waveform includes a characteristic tilt of between approximately 50% and 75%.

7. A system according to claim 6, wherein said second waveform includes a characteristic tilt of between approximately 50% and 75%.

8. A system according to claim 4, wherein said second includes an initial, relatively low amplitude step function and said second waveform has a characteristic tilt of between approximately 50% and 75%.

9. A system according to claim 8, wherein said second waveform comprises a second slow-rise waveform following said initial, relatively low amplitude step function.

10. A system according to claim 9, wherein said second slow-rise waveform is followed by an exponential decay portion which in turn is followed by a truncated portion.

11. A system according to claim 1, wherein said means for generating the slow-rise waveform includes a pulse-modulating circuit.

12. A system according to claim 1, wherein the exponential decaying portion of the slow-rise waveform comprises an unmodulated capacitor discharge time function.

13. A system according to claim 1, further comprising at least pair of defibrillation electrode assemblies electrically coupled to the system at a proximal end and electrically coupled to a portion of cardiac tissue near a distal end portion and wherein said pair of assemblies includes at least one of the following: a percutaneous electrode, a subcutaneous electrode, an epicardial electrode, an endocardial electrode, a pericardial electrode, a transcutaneous electrode, a surface electrode, a canister electrode, a coil electrode, a ring electrode.

14. A method of delivering at least one complex defibrillation waveform to a portion of cardiac tissue, comprising the steps:
    confirming the presence of a cardiac arrhythmia terminable by delivery of a defibrillation waveform;
    generating at least one pulse-modulated slow-rise defibrillation waveform portion until said slow-rise defibrillation waveform portion reaches a predetermined amplitude;
    allowing the amplitude of the defibrillation waveform to decay exponentially for either a predefined period of time or until a predetermined voltage threshold is reached;
    truncating said defibrillation waveform;
    providing said defibrillation waveform to a portion of cardiac tissue; and determining whether the cardiac arrhythmia has terminated, and if not, repeating the foregoing steps at a higher magnitude predetermined amplitude.

15. A method according to claim 14, further comprising the steps:
    after the truncating step, generating a second defibrillation waveform of opposite polarity to said at least one pulse-modulated slow-rise defibrillation waveform; and
    providing said second defibrillation waveform to the portion of cardiac tissue.

16. A method according to claim 15, wherein said second defibrillation waveform comprises an initial slow-rise defibrillation waveform portion.

17. A method according to claim 16, wherein said initial slow-rise defibrillation waveform portion is followed by an exponentially decaying portion, and said decaying portion if followed by a truncated portion.

18. A method according to claim 14, further comprising the initial step of generating a relatively low amplitude step function prior to generating the pulse-generated slow-rise defibrillation waveform, and wherein said pulse-generated slow-rise waveform is generated beginning from the relatively low amplitude step function.

19. A method according to claim 14, wherein a total duration of said defibrillation waveform includes a range of approximately 13 ms to approximately 28 ms.

20. A method according to claim 14, wherein said pulse-modulated slow-rise waveform is generated by a high speed, power switching converter.

21. A method according to claim 20, wherein the slow-rise defibrillation waveform includes one of a voltage-controlled waveform and a current-controlled waveform.

* * * * *